United States Patent [19]
Story et al.

[11] 3,967,619
[45] July 6, 1976

[54] APPARATUS AND METHOD FOR INTERMITTENT MANDATORY VENTILATION

[76] Inventors: Eddie W. Story, Rte. 2, Box 4, La Center, Wash. 98629; Jerald L. Liskey, 23300 W. Arata Road, No. 92, Troutdale, Oreg. 97060

[22] Filed: Nov. 15, 1974

[21] Appl. No.: 523,966

[52] U.S. Cl............................ 128/145.8; 128/188
[51] Int. Cl.² ........................................ A61M 16/00
[58] Field of Search............ 128/145.8, 145.5, 145.6, 128/145 R, 142, 142.2, 142.3, 2.08, 188, DIG. 17

[56] References Cited
UNITED STATES PATENTS

| | | | |
|---|---|---|---|
| 3,046,979 | 7/1962 | Andreasen........................ | 128/145.6 |
| 3,741,208 | 6/1973 | Jonsson et al. ................... | 128/145.6 |
| 3,865,106 | 2/1975 | Palush.............................. | 128/145.8 |

FOREIGN PATENTS OR APPLICATIONS

| | | | |
|---|---|---|---|
| 1,288,019 | 9/1972 | United Kingdom.............. | 128/145.6 |

OTHER PUBLICATIONS

Downs et al., Intermittent Mandatory Ventilation: A New Approach to Weaning Patients from Mechanical Ventilators; Mar. 26, 1972, Department of Anesthesiology, University of Florida College of Medicine.
Desautels et al., Respiratory Care, Mar., 1974, vol. 19, No. 3, pp. 187–191, Methods of Administering Intermittent Mandatory Ventilation (IMV).

*Primary Examiner*—Robert W. Michell
*Assistant Examiner*—Henry J. Recla
*Attorney, Agent, or Firm*—Chernoff & Vilhauer

[57] ABSTRACT

An apparatus and method for intermittent mandatory ventilation therapy utilizing a connecting device to interconnect an intermittent source of pressurized air, a less pressurized continuous source of air, and the respiratory system of a patient. The connecting device has a one-way bleed valve by which, in cooperation with other one-way valves, air from the continuous air source is prevented from entering an expiration tube through which the patient exhales. The bleed valve is placed in the supply tube from the continuous air source to "bleed off" to the surrounding atmosphere the supply of continuous air during patient expiration, thereby permitting a second one-way valve, also in the supply tube from the continuous air source, to close. By bleeding off the continuous air source during patient expiration, air pressure in the supply tube is prevented from overcoming the expiration pressure and forcing its way past the second one-way valve and into the patient's expiration tube, thereby ensuring that only patient exhalation enters the expiration tube. This allows the volumetric air flow through the expiration tube to be measured as a direct indication of the volumetric breathing rate of the patient. In addition, the one-way bleed valve prevents the introduction of air from the atmosphere into the supply tube from the continuous air source should the patient's inspirational demand momentarily exceed the output of the continuous air source. The connecting device mounts all one-way valves closely proximate the connection to the patient's respiratory system to minimize the amount of dead space in which the patient can exhale, and thereby minimizes the amount of exhalation that the patient can inhale during the succeeding inspiration. A second embodiment, aside from locating all valves still closer to the patient's connection, includes an additional one-way valve in the inspiration tube connecting the intermittent air source to the patient to prevent exhalation from entering the inspiration tube.

11 Claims, 6 Drawing Figures

U.S. Patent  July 6, 1976  3,967,619
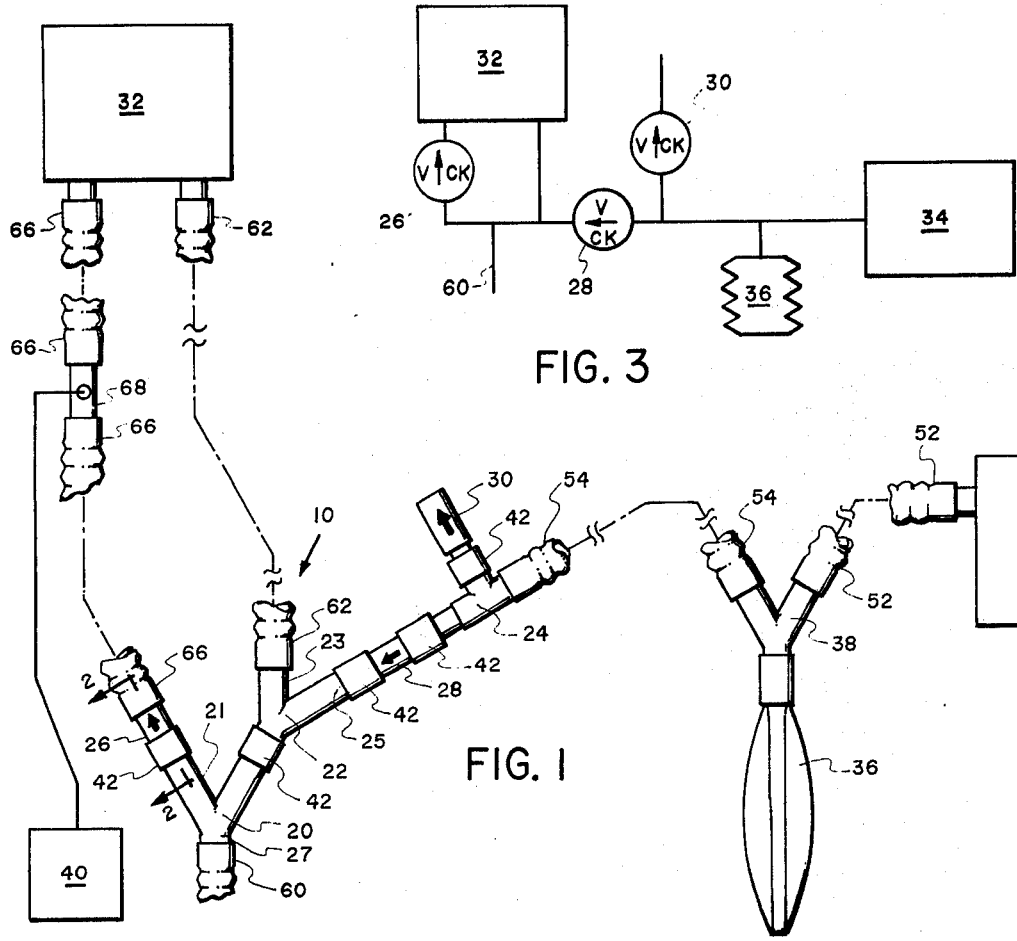
FIG. 3
FIG. 1
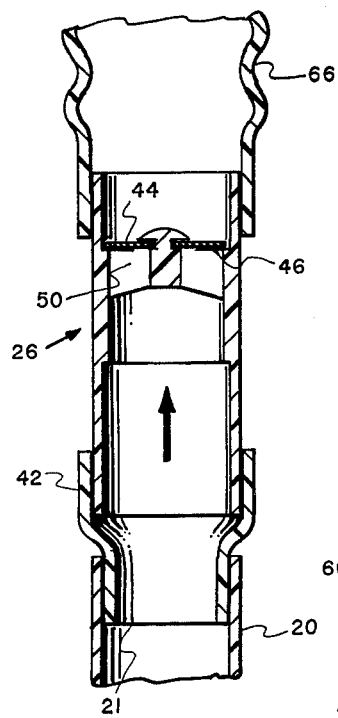
FIG. 2
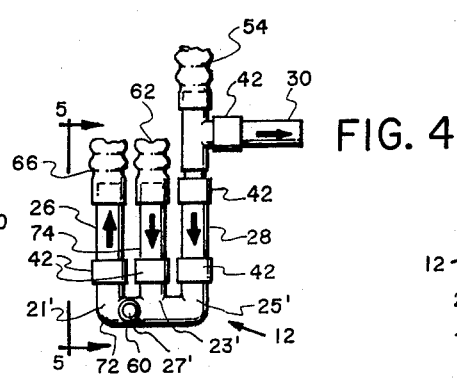
FIG. 4
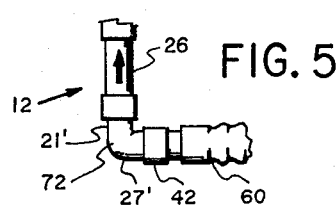
FIG. 5
FIG. 6

APPARATUS AND METHOD FOR INTERMITTENT MANDATORY VENTILATION

BACKGROUND OF THE INVENTION

The present invention relates to an attachment for a mechanical ventilator that permits a patient whose breathing is being assisted by the ventilator to be weaned therefrom. A mechanical ventilator is a device employed during the treatment of acute respiratory insufficiency to mechanically assist patient breathing by supplying a patient connected to the machine with a predetermined quantity of air at a predetermined pressure and at predetermined intervals. The patient may be connected to the machine via a trachael or tracheostomy tube or via a mask. The air supplied to the patient is usually ambient room air that has been enriched with oxygen and humidified by the ventilator. Typically, the selected volume of air is delivered to the patient at the beginning of each spontaneous inspiration or at fixed intervals if the patient's inspirational effort is insufficient to trigger the machine.

Ultimately, assuming normal patient recovery, the patient must be gradually disconnected from the ventilator and retaught to breathe spontaneously. For many patients, this "weaning" process is a very trying experience, one that they approach with much anxiety because of their fear of not being able to breathe without the assistance of the ventilator. For some patients, this anxiety and fear renders them uncooperative and unwilling to tolerate the often prolonged trials of spontaneous, unassisted breathing.

It was to solve this problem of patient weaning that the concept of intermittent mandatory ventilation (IMV) was developed. As disclosed in "Intermittent Mandatory Ventilation: A New Approach to Weaning Patients from Mechanical Ventilators" by John B. Downs et al., available from John B. Downs, M.D., NIH Research Fellow, Department of Anesthesiology, University of Florida College of Medicine, Gainesville, Florida, 32601, and "Methods of Administering Intermittent Mandatory Ventilation (IMV)," 19 Respiratory Care 187, March 1974, IMV is a method of automatic weaning whereby the ventilator is intermittently cycled to deliver a single volume of air to the patient at adjustably lengthening intervals. During the periods when air is not being supplied by the ventilator, the patient breathes spontaneously from a continuous alternate source of oxygen-enriched and humidified air. As the patient's spontaneous breathing improves, the periods between delivery of ventilator-supplied air are lengthened until, finally, the patient achieves continuous, unassisted, spontaneous breathing.

As disclosed in the second reference listed above, IMV systems are currently of two types: ambient reservoir and pressure reservoir. The ambient reservoir system employs a length of open-ended tubing to capture the air from the continuous source during periods of mandatory ventilation. The pressure reservoir system employs a small volume anesthesia bag in place of the length of open-ended tubing to capture and retain at a pressure slightly above ambient the air from the continuous source during the mandatory ventilation periods. In either system the captured air is available to the patient during spontaneous inspiration. However, with the ambient reservoir system there is a probability that the patient will inhale more air than the reservoir has captured and, therefore, an unknown quantity of non-oxygen-enriched and humidified air from the atmosphere. Such possibility is precluded by the pressure reservoir system.

To monitor the patient's progress during the weaning process, several physiological parameters must be continuously measured and analyzed. Among these parameters is the volume of air, known as the tidal volume, that is inspired and expired during each respiration. The usual method of measuring the tidal volume is to measure the volumetric flow through the patient's expiration tube. However, with the addition of the pressure reservoir to the continuous alternate air supply, the tidal volume cannot be determined accurately by measuring this volumetric flow because, during expiration, the expiration tube will contain air flowing from the alternate air source as well as the patient's exhalation. Consequently, the tidal volume measurement must presently be made by tapping the patient's connection tube close to the patient and before the tube branches into its expiration and inspiration components, such method being inconvenient and troublesome.

In addition, with current IMV valving and tubing arrangements which include one-way valves in both the expiration tube and the tube connecting the continuous alternate air supply to the patient, there is a substantial amount of "dead space" into which exhaled air from the patient can accumulate during each expiration. This exhaled air is then rebreathed during the next inspiration, decreasing the volume of oxygen-enriched air actually breathed by the patient and thus limiting the degree to which the quality of the air inspired by the patient can be controlled.

SUMMARY OF THE INVENTION

The present invention is directed to a unique connecting device and related system and method used to connect a patient both to a mechanical ventilator and to a continuous alternate air supply and associated pressure reservoir during intermittent mandatory ventilation (IMV) treatment. More particularly, the invention is directed to the addition of a one-way bleed valve to the tube connecting the alternate air supply to the patient, and to the unique location of other one-way valves to decrease dead space.

The mechanical ventilator is connected to the patient by an inspiration tube through which the patient receives air and by an expiration tube through which the patient exhales. A one-way valve is provided in the expiration tube to prevent the patient from inhaling previously exhaled air. The tube from the continuous source of air is tapped into the inspiration tube and contains its own one-way valve to prevent pressurized air from the ventilator or patient exhalation air from moving toward the continuous air source. The one-way bleed valve, when added to this valving and tubing system, serves to bleed off the slightly pressurized air from the continuous alternate air supply and pressure reservoir to the atmosphere during each patient expiration. Thus, as the patient exhales, the only air passing through the expiration tube is the patient's tidal volume, or that volume of air that was inhaled during inspiration. The advantage gained is that the patient's tidal volume can now accurately be measured and monitored anywhere along the expiration tube and especially at a distance removed from the patient's connection tube. This alleviates the need for additional apparatus and connections near the patient and relieves the discomfort to the patient caused by the apparatus hanging around and about his tracheal or other connection. The one-way structure of the bleed valve ensures that no untreated atmospheric air enters the continuous alternate air supply tube during spontaneous inspiration.

In one embodiment of the present invention, all valves between the patient and the ventilator and alternate air supply respectively are brought close to the patient's connection tube by means of a unique connecting device having five ports for joining all of the various inspiration, expiration and patient connection tubes, and housing all one-way valves in a central fitting located close to the patient. In an alternate embodiment, a more balanced and even more compact five-port connecting device is employed having an additional one-way valve near the port where the ventilator inspiration tube connects. This additional valve serves to prevent patient-exhaled air from entering the ventilator inspiration tube and being re-breathed by the patient during inspiration. In both embodiments, the close proximity of all of the one-way valves to the patient's connection tube minimizes the volume of dead space in which patient-exhaled air can accumulate, thus permitting a greater degree of control over the oxygen content, humidity and other characteristics of the air actually inhaled during each inspiration.

It is, therefore, a principal objective of the present invention to provide a connecting device, system and method for use during IMV therapy that prevents the introduction of air from the alternate air supply and its associated pressure reservoir into the ventilator expiration tube during patient expiration.

It is an additional objective of the present invention to provide a connecting device, systems and method for use during IMV therapy which controls closely the characteristics of the air breathed by the patient by minimizing the volume of dead space into which patient-exhaled air can accumulate during expiration and thereafter be re-inhaled, and by preventing the uncontrolled entry of atmospheric air into the system during inspiration.

It is a further objective of the present invention to provide such a connecting device that prevents the introduction of patient exhaled air into the ventilator inspiration line during patient expiration.

The foregoing objectives, features and advantages of the present invention will be more readily understood upon consideration of the following detailed description of the invention taken in conjunction with the accompanying drawings.

BRIEF DESCRIPTION OF THE DRAWINGS

FIG. 1 is a semi-schematic, extended view of the IMV system of the present invention showing one embodiment of the connecting device.

FIG. 2 is a detail sectional view of a typical tubular one-way valve taken along line 2—2 of FIG. 1.

FIG. 3 is a schematic diagram of the embodiment of the IMV system shown in FIG. 1.

FIG. 4 is an elevation of an alternate embodiment of the connecting device of the present invention.

FIG. 5 is a side view of the alternate embodiment of the connecting device of FIG. 4.

FIG. 6 is a schematic diagram of the alternate embodiment of the IMV system shown in FIG. 4.

DETAILED DESCRIPTION OF THE INVENTION

Referring to FIG. 1, one embodiment of the connecting device of the present invention, designated generally as 10, is seen to comprise two Y-shaped tubular members 20 and 22 interconnected to form a tubular assembly having four ports 21, 23, 25 and 27, a T-shaped tubular member 24, and three one-way check-valves 26, 28 and 30 coupled together as shown in the figure. The connection device 10 is employed to interconnect the components of a mechanical ventilating system including a ventilator 32 which provides an intermittent source of pressurized air through an inspiration tube 62 and a path for patient exhalation through an expiration tube 66, a continuous source of less pressurized air shown collectively as air source 34, and air reservoir 36 with its interconnecting Y-shaped tubular member 38, and a volume-measuring device 40. The various components of the connective device 10 are joined by a plurality of tubular connecting members 42.

One-way valves 26, 28 and 30 are simple flapper valves as shown in FIG. 2 with a resilient disc-shaped flapper 44 biased slightly to the closed position whereby, when the differential pressure on the sides of the resilient flapper 44 is in the direction of the arrow, the pressure pushes the flapper 44 away from its annular seat 46 and air passes through the valve body. Differential pressure in the opposite direction causes flapper 44 to press firmly against its annular seat 46, thereby preventing air from passing. Flapper 44 is supported within the valve body by an apertured supporting member 50 which attaches to the interior walls of the valve body and extends through the center of the flapper.

Returning to FIG. 1, the intermittent air source can be provided through tube 62 by any conventional mechanical ventilator 32 that is capable of delivering a preselected volume of oxygen-enriched, humidified air at a preselected pressure and at preselected intervals. The continuous air source 34 can be any conventional unit capable of delivering a continuous supply of similarly oxygen-enriched, humidified air at a preselected pressure substantially lower than the delivery pressure of the ventilator 32. Reservoir 36 is employed in conjunction with the continuous air source 34 to ensure that sufficient oxygen-enriched and humidified air will always be available for spontaneous breathing by the patient. Y-shaped member 38 is a readily available connector designed to ensure that air entering the connector from tube 52 will enter and fill reservoir 36 before exiting via tube 54. Thus, reservoir 36 will always contain oxygen-enriched and humidified air at a pressure equal to that of the air supplied by air source 34. Also included in Y-shaped member 38 but not shown in the drawings is a one-way check-valve for allowing air to be drawn into line 54 from the atmosphere should the air source 34 or reservoir 36 fail during operation.

For use during intermittent mandatory ventilation (IMV) therapy, ventilator 32 should be initially adjusted to deliver 12 to 15 ml/kg of oxygen-enriched and humidified air every six to ten seconds at a pressure of 30 to 60 cm $H_2O$. Similarly, continuous air source 34 should be adjusted to deliver a continuous flow of identically oxygen-enriched and humidified air at a pressure of less than 5 cm $H_2O$. The major function of air source 34 is to supply a controlled atmosphere rather than a high pressure.

In operation, with the system components adjusted as described above and interconnected as shown in FIG. 1 and the schematic diagram of FIG. 3, and lower port 27 of Y-shaped member 20 connected to a patient's respiratory system via a flexible patient connection tube 60, intermittent volumes of air are delivered to the patient via inspiration tube 62 and continuous air is supplied via tube 54 for spontaneous breathing. The arrows on the one-way check valves in the figures indicate the direction of free air passage. Because of the pressure differential between the intermittent air supply and the continuous air supply, whenever a volume of intermittent air is being supplied, one-way valve 28 closes, thereby forcing the air from the ventilator 32 to be routed into the patient's lungs via Y-shaped members 22 and 20 and the patient's tube 60. A separate conventional valve within the ventilator 32 (not shown) automatically and simultaneously seals expiration tube 66 and prevents the intermittent air from bypassing the patient and exiting via tube 66. At the termination of the intermittent air pulse, the valve within the ventilator 32 opens and allows the patient to exhale through one-way valve 26 and expiration tube 66. A volume sensing device 68 is located in the expiration tube 66 and connected to volume monitor 40 to produce a continuous record of the volume of air exhaled by the patient during each expiration.

Between the pulses of air from the ventilator 32, inspiration tube 62 is effectively sealed within the ventilator and the patient is allowed to breath spontaneously by drawing air from reservoir 36 and continuous air source 34 via supply tube 54. During spontaneous inspiration, check-valve 26 closes to prevent inhalation of the previously exhaled air in tube 66, and check-valve 28 opens allowing the patient to draw air from the continuous source 34.

During each expiration, whether after a pressurized inspiration initiated by ventilator 32 or after a spontaneous inspiration from source 34, the presence of a one-way bleed valve 30 a T-shaped member 24 ensures that check-valve 28 closes during expiration and thus prevents the entrance into Y-shaped member 22 of air from the continuous air source. The bleed valve 30 accomplishes this action by preventing a build-up of pressure in tube 54 sufficient to overcome the patient's expiration pressure which tends to close valve 28. This important inter-action of check-valves 28 and 30, in turn, ensures that volume monitor 40 will record only the volume of air exhaled by the patient. Without the one-way bleed valve 30, the pressure in tube 54 would overcome the opposing pressure of the patient's expiration and would open valve 28, thereby adding volume from continuous source 34 to the patient's expiration volume flowing through expiration tube 66 and thus causing volume monitor 40 to produce a false tidal volume reaading. Because of the unique inter-action between valves 28 and 30, the volume detecting device 68 may be located anywhere along expiration tube 66 as is rather than in the patient's connection tube 60 as is necessary with prior art pressure-reservoir-type IMV systems. During spontaneous inspirations, the one-way character of bleed valve 30 prevents untreated atmospheric air from entering line 54 and being inspired by the patient.

In an alternate embodiment of the connecting device, designated generally as 12 in FIGS. 4 and 5, a specially-shaped, balanced tubular member 72 having three ports 21', 23', and 25' spaced side-by-side and facing in the same general direction and a fourth port 27' facing in a direction different from that of the other three ports is substituted for the two Y-shaped members 20 and 22 of FIG. 1 such that all valves are located very proximate to the patient's connection tube 60 attached to port 27'. Also, an additional one-way valve 74 of the same type as previously described is added to seal the inspiration tube 62 closer to the patient during expiration as indicated in the figures and the schematic diagram of FIG. 6. When the ventilator 32 is delivering the preselected volume of air, valve 74 opens causing one-way valve 28 to close as before. Also as before, the valve within the ventilator effectively seals expiration tube 66. At the end of the intermittent air pulse, expiration tube 66 is effectively unsealed, and the patient exhales via the expiration tube 66 while valve 74 closes due to the reversed pressure differential caused by expiration. All other valves operate as before.

The advantage gained by adding check-valve 74 and locating all valves very close to the patient's connection tube 60 by employing the alternate connection device 12 is that any exhalation that does not exit via expiration tube 66 is confined to a relatively small space in the tubular member 72, thereby minimizing the dead space and thus the amount of exhaled air that the patient can re-breathe during the next inspiration. This improves the control over the amount and quality of oxygen-enriched air actually breathed.

The terms and expressions which have been employed in the foregoing abstract and specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A device for connecting to a patient the components of an intermittent mandatory ventilation system of the type including an intermittent source of pressurized air having inspiration and expiration tubes respectively, a volume measuring means connected to said expiration tube for measuring the volume of air exhaled by said patient and a continuous separate source of pressurized air, said device comprising:
 a. a tubular assembly having means defining five interconnected ports, a first port of which is for connecting to the respiratory system of a patient, a second port of which is for connecting to the inspiration tube of said intermittent source of pressurized air, a third port of which is for connecting to the expiration tube of said intermittent air source, and a fourth port of which is for connecting to said continuous air source;
 b. first one-way valve means mounted within said tubular assembly between said first and third ports for permitting air to flow from said first port to said third port while preventing a reverse flow of said air;
 c. second one-way valve means mounted within said tubular assembly separating said first, second and third ports respectively from said fourth port and responsive to the differential-pressure on either side of said second valve means permitting air to flow from said fourth port toward said first, second and third ports when patient-generated inspiration pressure is less than the pressure at said fourth port by a predetermined amount, and for preventing a reverse flow of said air;

d. said fifth port of said tubular assembly being positioned on the same side of said second one-way valve means as said fourth port and having a third one-way valve means associated therewith responsive to the pressure at said fourth port for permitting air to flow from within said tubular assembly outwardly through said fifth port during patient expiration so as to prevent the pressure at said fourth port from exceeding patient-generated expiration pressure by said predetermined amount, and thereby prevent air flow from said fourth port through said second valve means toward said first, second and third ports during patient expiration, said third one-way valve means also including means for preventing a reverse flow of said air through said fifth port.

2. The device of claim 1 wherein said tubular assembly includes a first tubular, Y-shaped element having means defining said first and third ports, a second tubular, Y-shaped element connected to said first Y-shaped element having means defining said second port, and a T-shaped tubular element connected to said second Y-shaped element having means defining said fourth and fifth ports.

3. The device of claim 1 wherein each of said one-way valve means is biased toward the closed position.

4. The device of claim 3 wherein each of said one-way valve means comprises a one-way tubular flapper valve of substantially circular cross section with a resilient flapper biased toward the closed position.

5. The device of claim 1, further comprising a fourth one-way valve means mounted within said tubular assembly between said first and second ports for permitting air to flow from said second port to said first port while preventing a reverse flow of said air.

6. The device of claim 5 wherein said tubular assembly includes a tubular member having said second, third and fourth ports formed therein positioned side-by-side and facing generally in the same direction and also having said first port formed therein facing in a different direction from said second, third and fourth ports.

7. An intermittent mandatory ventilation system for a patient, comprising:
a. an intermittent source of pressurized air having inspiration and expiration tubes respectively;
b. a continuous source of pressurized air;
c. first conduit means for conducting air from the inspiration tube of said intermittent source of pressurized air to the respiratory system of the patient;
d. second conduit means for conducting air from the respiratory system of said patient to the expiration tube of said intermittent source of pressurized air.
e. volume measuring means connected to said expiration tube for measuring the volumetric flow rate of air flowing through said expiration tube;
f. first valve means within said second conduit means for permitting air to flow from said patient to said expiration tube while preventing air from flowing from said expiration tube to said patient;
g. third conduit means interconnected in parallel relationship with said first and second conduit means for conducting air from said continuous source of pressurized air to the respiratory system of said patient;
h. second valve means within said third conduit means separating said first and second conduit means respectively from said third conduit means and responsive to the differential-pressure on either side of said second valve means for permitting air to flow from said continuous source of pressurized air to said patient when patient-generated inspiration pressure is less than the pressure in said third conduit means by a predetermined amount, and for preventing air from flowing from said patient to said continuous source of pressurized air; and
i. third valve means attached to said third conduit means between said second valve means and said continuous source of pressurized air responsive to the pressure in said third conduit means for permitting air to flow from said third conduit means to the atmosphere during patient expiration so as to prevent the pressure in said third conduit means from exceeding patient-generated expiration pressure by said predetermined amount, and thereby prevent air flow from said continuous source of pressurized air through said second valve means to said second conduit means during patient expiration, and for preventing air from flowing from the atmosphere to said third conduit means so as to prevent atmospheric air flow through said second valve means during patient inspiration.

8. The system of claim 7 wherein the pressure of the air from said intermittent source of pressurized air is substantially greater than the pressure of the air from said continuous source of pressurized air.

9. The system of claim 7, further comprising fourth valve means within said first conduit means for permitting air to flow from said inspiration tube to said patient while preventing air from flowing from said patient to said inspiration tube.

10. The system of claim 7 wherein each of said valve means is biased toward the closed position.

11. The system of claim 10 wherein each of said valve means comprises a one-way tubular flapper valve of substantially circular cross-section with a resilient flapper biased toward the closed position.

* * * * *